US010368978B2

(12) United States Patent
Hyun

(10) Patent No.: US 10,368,978 B2
(45) Date of Patent: Aug. 6, 2019

(54) ADJUSTABLE INTRAOCULAR LENS

(71) Applicant: Dong Won Hyun, Seongnam-si (KR)

(72) Inventor: Dong Won Hyun, Seongnam-si (KR)

(73) Assignee: Dong Won Hyun (KR)

( * ) Notice: Subject to any disclaimer, the term of this patent is extended or adjusted under 35 U.S.C. 154(b) by 0 days.

(21) Appl. No.: 15/751,898

(22) PCT Filed: Aug. 9, 2016

(86) PCT No.: PCT/KR2016/008747
§ 371 (c)(1),
(2) Date: Feb. 12, 2018

(87) PCT Pub. No.: WO2017/026771
PCT Pub. Date: Feb. 16, 2017

(65) Prior Publication Data
US 2018/0228601 A1 Aug. 16, 2018

(30) Foreign Application Priority Data

Aug. 13, 2015 (KR) .......... 10-2015-0114569
Aug. 9, 2016 (KR) .......... 10-2016-0101224

(51) Int. Cl.
*A61F 2/16* (2006.01)
(52) U.S. Cl.
CPC .......... *A61F 2/1627* (2013.01); *A61F 2/1616* (2013.01); *A61F 2002/169* (2015.04);
(Continued)

(58) Field of Classification Search
CPC ...... A61F 2/1659; A61F 2/1627; A61F 9/007; A61F 9/013; A61F 2002/169;
(Continued)

(56) References Cited

U.S. PATENT DOCUMENTS 4,778,462 A 10/1988 Grendahl
7,926,940 B2 4/2011 Blum et al.
(Continued)

FOREIGN PATENT DOCUMENTS

JP 3677040 5/2005
KR 20100114133 10/2010
(Continued)

OTHER PUBLICATIONS

International Search Report, International Application No. PCT/KR2016/008747, dated Oct. 31, 2016.
(Continued)

*Primary Examiner* — David H Willse
*Assistant Examiner* — Tiffany P Shipmon
(74) *Attorney, Agent, or Firm* — Perman & Green, LLP

(57) ABSTRACT

An adjustable intraocular lens which allows external light to be selectively transmitted therethrough. The adjustable intraocular lens includes, a lens body having a front surface, a rear surface, and a central optical part convexly formed in a first direction, a plurality of support parts extending in a radial direction at the edge of the lens body, and an optical fiber part which is disposed on the outside of the central optical part and surrounds the central optical part.

18 Claims, 13 Drawing Sheets

(52) U.S. Cl.
 CPC ........... *A61F 2002/1681* (2013.01); *A61F 2002/16901* (2015.04); *A61F 2250/0053* (2013.01)

(58) Field of Classification Search
 CPC ... A61F 2002/16901; A61F 2002/1696; G02C 7/165
 See application file for complete search history.

(56) References Cited

U.S. PATENT DOCUMENTS

| | | | |
|---|---|---|---|
| 9,389,433 | B2 | 7/2016 | Pugh et al. |
| 2004/0184158 | A1 | 9/2004 | Shadduck |
| 2008/0077238 | A1 | 3/2008 | Deacon et al. |
| 2009/0088840 | A1 | 4/2009 | Simpson et al. |
| 2011/0040376 | A1* | 2/2011 | Christie ............... A61F 2/1613 623/6.17 |
| 2014/0277437 | A1 | 9/2014 | Currie |
| 2016/0262876 | A1* | 9/2016 | DeBoer ............... A61F 2/1659 |

FOREIGN PATENT DOCUMENTS

| | | |
|---|---|---|
| KR | 20120093837 | 8/2012 |
| KR | 20140113447 | 9/2014 |
| WO | 9506446 | 3/1995 |
| WO | 0052516 | 9/2000 |
| WO | 2011020078 | 2/2011 |

OTHER PUBLICATIONS

Korean Office Action, Korean Application No. 10-2016-0101224, dated Oct. 19, 2016.
Korean Office Action, Korean Application No. 10-2016-0101224, dated Jun. 16, 2017.
Japanese Office Action, Japanese Application No. 2018-513271, dated Jul. 3, 2018.
Extended European Search Report, European Application No. 16835411.6, dated Mar. 12, 2019.

\* cited by examiner

ADJUSTABLE INTRAOCULAR LENS

CROSS REFERENCE TO RELATED APPLICATIONS

This application is the National Stage of International Application No. PCT/KR2016/008747, having an International Filing Date of 9 Aug. 2016, which designated the United States of America, and which International Application was published under PCT Article 21(2) as WO Publication No. 2017/026771 A1, and which claims priority from and the benefit of Korean Patent Application No. 10-2015-0114569, filed on 13 Aug. 2015, and Korean Patent Application No. 10-2016-0101224, filed on 9 Aug. 2016, the disclosures of which are incorporated herein by reference in their entireties.

BACKGROUND

1. Field

The presently disclosed embodiment relates to an intraocular lens, and more particularly, an adjustable intraocular lens that is implanted in a human eye.

2. Brief Description of Related Developments

Generally, an intraocular lens (IOL) refers to an artificial lens that is implanted in an eye to replace an opaque lens of a cataract patient.

Intraocular lens (artificial lens) insertion is a method of extracting a cataract from a patient and inserting an intraocular lens made of an artificial material into an eye as an alternative so as to replace the role of glasses or a contact lens after surgery. The intraocular lens insertion is currently implemented in many places around the world.

A cataract is a disease in which the lens of the eye becomes opaque, the outside light cannot be clearly focused on the retina, and thus the visual acuity is reduced. In order to treat this disease, it is common to remove an opaque lens inside a lens capsule and perform an operation of inserting an intraocular lens made of various materials that do not cause complications such as inflammation when inserted into the eye.

Research on the shape or material of an intraocular lens has continued with respect to implanting an intraocular lens so that a patient can clearly see a close or distant object. For example, there is a method of injecting a liquid, such as water, into an intraocular lens to perform a multifocal function or a method of changing a shape of an intraocular lens so as to adjust a focus.

U.S. Patent Publication No. 2009-0088840 (entitled ZONAL DIFFRACTIVE MULTIFOCAL INTRAOCULAR LENSES) discloses a technique for forming a refractive region on a surface of a lens so as to provide a multifocal intraocular lens.

SUMMARY

Aspects of the presently disclosed embodiment provide adjustable intraocular lenses that align light incident on an intraocular lens so as to improve visibility.

An aspect of the presently disclosed embodiment provides an adjustable intraocular lens including: a lens body having a front surface and a rear surface and comprising a central optic zone formed convexly in a first direction; a plurality of support portions extending from an edge of the lens body in a radial direction; and an optical rod arranged so that at least part thereof is included inside the central optic zone and the optical rod surrounds an outer portion of the central optic zone.

An adjustable intraocular lens according to an aspect of the presently disclosed embodiment may transmit light incident on a central optic zone, but selectively transmit light incident on an optical rod, thereby forming a clearer image. The optical rod may align incident light, thereby improving the depth of focus. In addition, the adjustable intraocular lens may adjust the amount of light passing through the central optic zone, thereby adjusting the brightness of an image formed on a retina. The scope of the presently disclosed embodiment is not limited by such effects.

DETAILED DESCRIPTION

Figure 1:
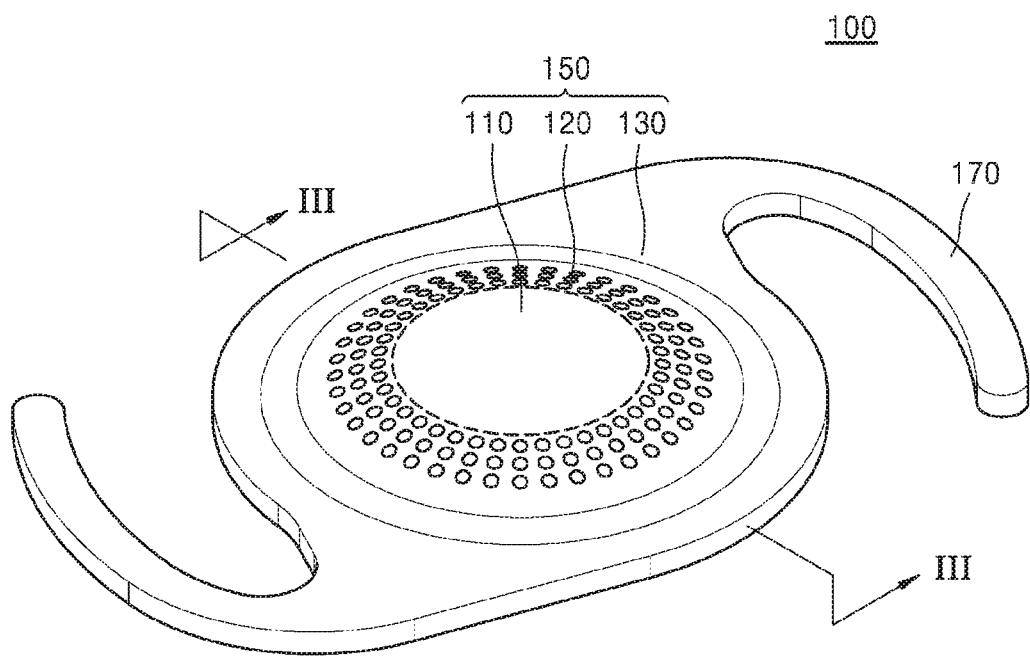
FIG. 1 is a perspective view illustrating an adjustable intraocular lens according to an aspect of the presently disclosed embodiment.

An aspect of the presently disclosed embodiment provides an adjustable(accommodative) intraocular lens including: a lens body having a front surface and a rear surface and including a central optic zone formed convexly in a first direction; a plurality of support portions extending from an edge of the lens body in a radial direction; and an optical rod arranged so that at least part thereof is included inside the central optic zone and the optical rod surrounds an outer portion of the central optic zone.

A refractive index of the optical rod may be different from a refractive index of the central optic zone.

The optical rod may be arranged so that a length direction of the optical rod and the first direction form a predetermined angle.

The lens body may include: a transition zone which surrounds the central optic zone and in which the optical rod is arranged; and an edge zone which surrounds the transition zone and to which the plurality of support portions are connected.

A thickness of the transition zone in the first direction may be gradually reduced from the central optic zone toward the edge zone.

The optical rod may include: a first rod portion arranged adjacent to the central optic zone; and a second rod portion arranged adjacent to the first rod portion in a radial direction.

An angle formed by the length direction of the first rod portion and the first direction may be less than an angle formed by a length direction of the second rod portion and the first direction.

A plurality of optical rods may be arranged in a radial direction of the central optic zone, and diameters of the optical rods may be reduced in the radial direction.

The optical rod may extend from the front surface to the rear surface of the lens body.

The optical rod may be inserted into the front surface or the rear surface of the lens body.

The optical rod may be arranged inside the lens body.

The optical rod may be arranged adjacent to the front surface rather than the rear surface of the lens body, or may be arranged adjacent to the rear surface rather than the front surface of the lens body.

An outer wall of the optical rod may be tapered in the first direction.

The optical rod may include at least one of a glass rod or an optical fiber.

At least some of external light incident on the optical rod may be totally reflected from an inner wall of the optical rod. External light directed toward the central optic zone may pass through the central optic zone, and the external light directed toward the optical rod may selectively pass through the optical rod according to an incident angle.

A light absorbing coating may be applied to an outer wall of the optical rod.

Aspects of the disclosed embodiment will now be described more fully hereinafter with reference to the accompanying drawings; however, they may be embodied in different forms and should not be construed as limited to the aspects set forth herein. Rather, these aspects are provided so that this disclosure will be thorough and complete, and will fully convey exemplary implementations to those skilled in the art. The scope of the presently disclosed embodiment is defined by the appended claims. The terminology used herein is for the purpose of describing particular aspects only, and is not intended to be limiting. An expression used in the singular encompasses the expression in the plural, unless it has a clearly different meaning in the context. It will be understood that the terms "comprises," "includes," "including," and/or "comprising," when used in this specification, specify the presence of stated components, steps, operations, and/or elements, but do not preclude the presence or addition of one or more other components, steps, operations, and/or elements. While the terms as "first," "second,", and the like, may be used to describe various components, such components must not be limited to the above terms. The above terms are used only to distinguish one component from another.

Figure 2:
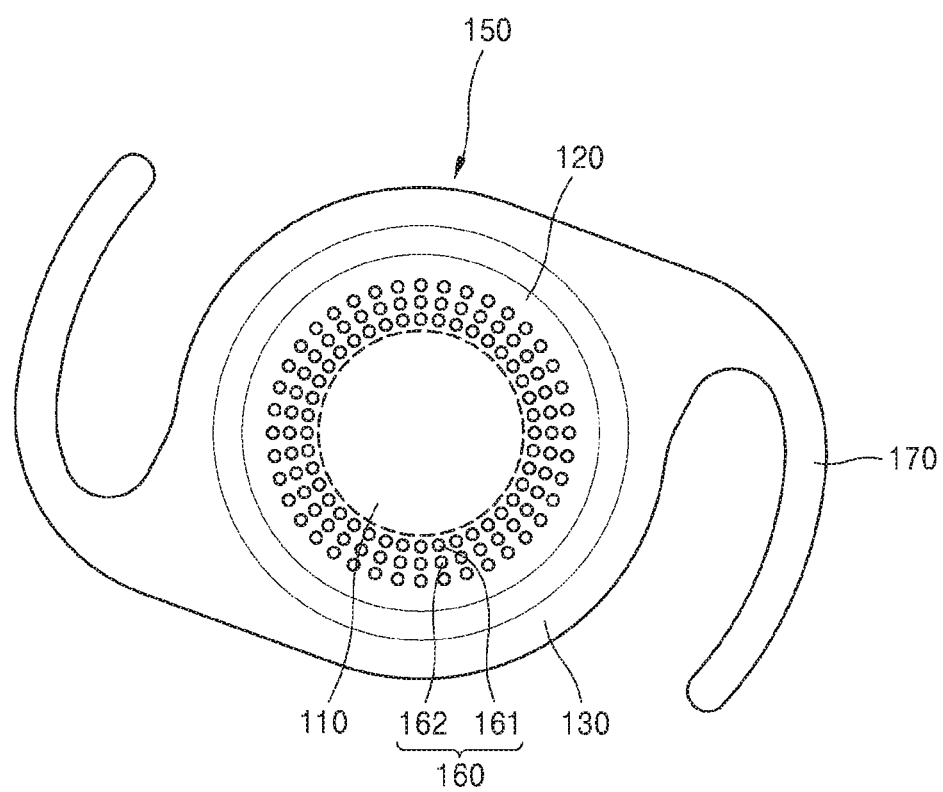
FIG. 2 is a plan view illustrating the adjustable intraocular lens of FIG. 1.
Figure 3:
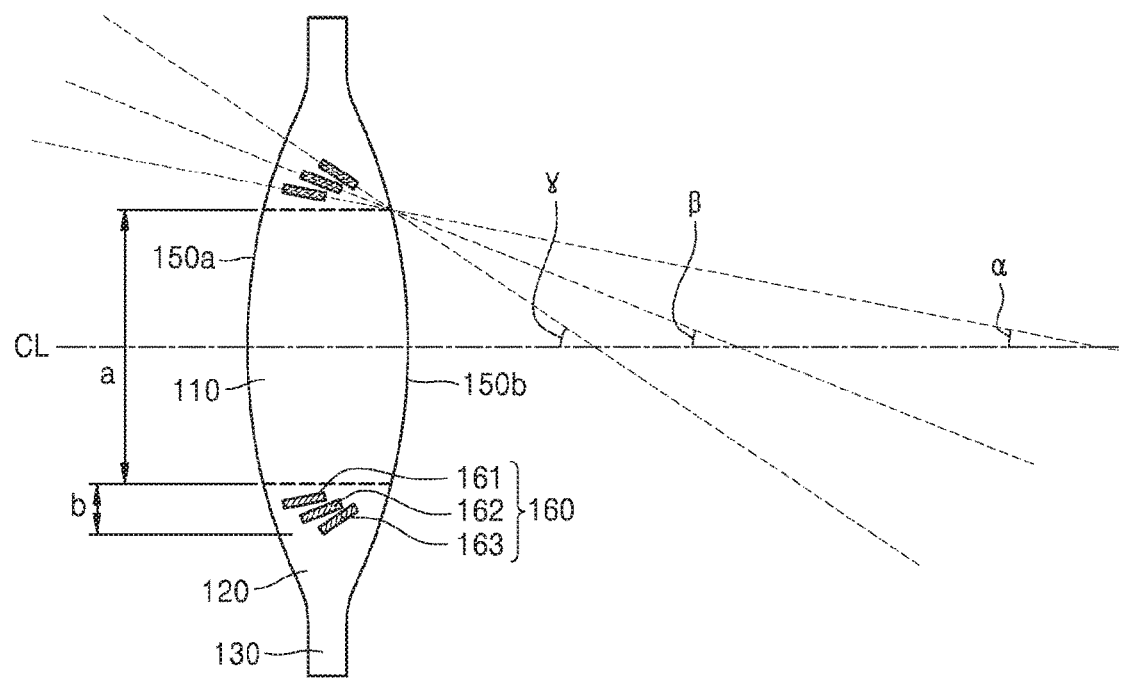
FIG. 3 is a cross-sectional view taken along a line III-III of FIG. 1.

FIG. 1 is a perspective view illustrating an adjustable intraocular lens 100 according to an aspect of the presently disclosed embodiment, FIG. 2 is a plan view illustrating the adjustable intraocular lens 100 of FIG. 1, and FIG. 3 is a cross-sectional view taken along a line III-III of FIG. 1.

Referring to FIGS. 1 to 3, the adjustable intraocular lens 100 may include a lens body 150, an optical rod 160, and a support portion 170. The adjustable intraocular lens 100 may be implanted in a region from which all or part of a natural lens (17 in FIG. 10A) of a human eye is removed.

Hereinafter, an incident angle of light incident on the adjustable intraocular lens 100 is defined as an angle between a direction of a center line CL in a thickness direction of the adjustable intraocular lens 100 and a direction of incident light. Therefore, that the incident angle is small means that light is almost vertically incident on the adjustable intraocular lens 100, and that the incident angle is large means that light is incident toward the adjustable intraocular lens 100 from the side of the adjustable intraocular lens 100.

The lens body 150 may have a front surface 150a and a rear surface 150b. The front surface 150a corresponds to a region on which external light is incident. The rear surface 150b corresponds to the front surface 150a and corresponds to a region coming into contact with a human's lens capsule or facing a direction toward a human's retina. External light may enter the front surface 150a, move through the lens body 150, and pass through the rear surface 150b.

The lens body 150 may include a central optic zone 110, a transition zone 120 in which the optical rod 160 is disposed, and an edge zone 130. The lens body 150 is a region through which external light transmits and is generally used as an optic.

The lens body 150 may include a relatively hard material, a relatively soft, bendable semi-rigid material, or a combination of the hard material and the soft material. For example, the lens body 150 may include polymethyl methacrylate (PMMA), polysulfone (PSF), or other relatively hard, biologically inert optical materials. In addition, the lens body 150 may include a silicone resin, hydrogel, thermolabile materials, and other flexible, semi-rigid, biologically inert optical materials.

The central optic zone 110 may be convex in a first direction that is a thickness direction of the lens body 150. The front surface 150a of the central optic zone 110 may be convex in the first direction, or the rear surface 150b of the central optic zone 110 may be convex in the first direction. In addition, as illustrated in FIG. 3, both the front surface 150a and the rear surface 150b may be convex. Hereinafter, for convenience of description, a case where both the front surface 150a and the rear surface 150b are convex will be described.

The central optic zone 110 may be arranged at the center of the lens body 150. The central optic zone 110 can accommodate most of external light incident on the adjustable intraocular lens 100. The central optic zone 110 may be aligned with the macula when the adjustable intraocular lens 100 is implanted in the human eye.

The transition zone 120 may surround the central optic zone 110, and the optical rod 160 may be arranged in the transition zone 120. The transition zone 120 may be formed such that the thickness of the transition zone 120 in the first direction decreases from the central optic zone 110 to the edge zone 130. In addition, a predetermined groove may be formed in the transition zone 120, so that the central optic zone 110 and the edge zone 130 may be distinguished from each other.

The edge zone 130 may surround the transition zone 120, and a plurality of support portions 170 may be connected to the edge zone 130. The edge zone 130 may have a circular shape as illustrated in FIG. 2. However, the shape of the edge zone 130 is not limited thereto, and a portion to which the support portion 170 is connected may be flat.

The optical rod 160 may be arranged to surround the outer portion of the central optic zone 110. The optical rod 160 may be arranged such that at least some of the optical rod 160 is included inside the central optic zone 110. The optical rod 160 may extend in the first direction. In addition, the cross-section of the optical rod 160 may be polygonal or circular. For example, the optical rod 160 may have a substantially polygonal column shape or a substantially circular column shape.

A plurality of optical rods 160 may be arranged around the central optic zone 110 to form a ring shape. In addition, a plurality of the optical rods 160 may be arranged in a radial direction from the central optic zone 110. The optical rods 160 may be partially overlapped and continuously arranged to each other. In addition, the optical rods 160 may be arranged with a predetermined interval therebetween. Hereinafter, for convenience of description, a case where three optical rods 160 are regularly arranged with a predetermined interval will be described.

Specifically, the optical rod 160 may include a first rod portion 161 adjacent to the central optic zone 110 and arranged in a circular shape around the central optic zone 110, a second rod portion 162 arranged on the outside in the radial direction of the first rod portion 161, and a third rod portion 163 arranged on the outside in the radial direction of the second rod portion 162.

The first rod portion 161, the second rod portion 162, and the third rod portion 163 may extend from the front surface 150a to the rear surface 150b, respectively.

A longitudinal direction of each optical rod 160 may have a predetermined angle with the first direction. The optical rod 160 may form a predetermined angle with the center line CL of the central optic zone 110. In addition, the angle may increase in proportion to the radial direction relative to the central optic zone 110. The optical rod 160 is arranged to have a predetermined angle so that, when light having a large incident angle is incident, the light can be reflected by a sidewall of the optical rod 160. At this time, the optical rod 160 has a slope and can increase the incidence area, thereby effectively aligning light.

Specifically, the longitudinal direction of the first rod portion 161 and the center line CL of the central optic zone 110 form a first angle (α), the longitudinal direction of the second rod portion 162 and the center line CL of the central optic zone 110 form a second angle (β), and the longitudinal direction of the third rod portion 163 and the center line CL of the central optic zone 110 form a third angle (γ). The third angle is greater than the second angle and greater than the first angle. In addition, the second angle is greater than the first angle. Furthermore, the optical rod 160 may be arranged so that the arrangement angle becomes smaller toward the radial direction from the center line CL.

Figure 4:
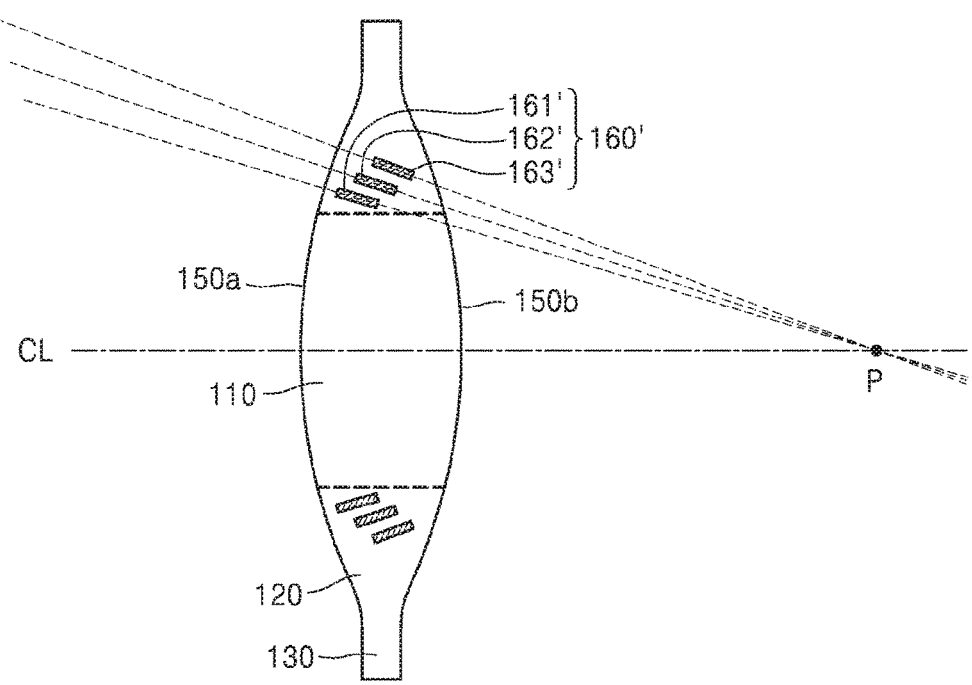
FIG. 4 is a cross-sectional view illustrating a modification of the adjustable intraocular lens of FIG. 1.

FIG. 4 is a cross-sectional view illustrating a modification of the adjustable intraocular lens 100 of FIG. 1.

Referring to FIG. 4, a longitudinal center of an optical rod 160' may be formed in one region P. Longitudinal extension lines of the first rod portion 161', a second rod portion 162', and a third rod portion 163' may be arranged to be collected in one region P. The optical rod 160' may converge external light into one region to secure the field of view.

Referring to FIG. 3 again, a length b of a region in which the optical rod 160 is arranged may be less than a diameter a of the central optic zone 110. Most of light incident from the outside passes through the central optic zone 110, and only part of light having a large incident angle is reflected by the optical rod 160 to align the light. Hereinafter, the incident angle is an angle between the first direction and the moving direction of the light. A detailed description thereof will be described below.

A refractive index of the optical rod 160 may be different from a refractive index of the central optic zone 110. For example, the refractive index of the optical rod 160 may be greater than the refractive index of the central optic zone 110, or the refractive index of the optical rod 160 may be less than the refractive index of the central optic zone 110. Thus, the light incident on the optical rod 160 may be selectively transmitted according to the incident angle. For example, the optical rod 160 may be selected from one of an optical fiber material and a glass fiber material.

The support portion 170 may extend from the edge zone 130 of the lens body 150 in the radial direction. A plurality of support portions 170 may be provided, and the support portion 170 is typically used as a haptic.

The support portion 170 can prevent the lens body 150 from moving or rotating within the eyeball. That is, the support portion 170 may be supported on the inner surface of the eye, such as being inserted inside the remnant lens capsule or being inserted in the sulcus between the ocular zonules and the iris, so that the lens body 150 may be arranged in the optical path of the eye. The support portion 170 may have various shapes and sizes according to a position at which the adjustable intraocular lens 100 is implanted. For example, the support portion 170 may have a C-shape, a J-shape, a U-shape, a flat design, or other designs. Hereinafter, for convenience of description, a case where two support portions 170 extend from the edge zone 130 will be described. FIGS. 5A to 5F are cross-sectional views illustrating another modification of the adjustable intraocular lens 100 of FIG. 1. Modifications of the adjustable intraocular lens 100 are characteristically different in terms of the structure and arrangement of the optical rod which will be mainly described below Referring to FIG. 5A, an optical rod 160a may be inserted to connect a front surface 150a to a rear surface 150b. A first rod portion 161a and a second rod portion 162a may extend in the first direction from the front surface 150a toward the rear surface 150b.

The optical rod 160a may partially pass external light incident on a transition zone 120 of the front surface 150a. The optical rod 160a may reflect part of incident light and may pass part of the incident light according to a refractive index of the optical rod 160a. In addition, when an incident angle of the external light is equal to or greater than a critical angle of the optical rod portion 160a, the optical rod 160a may reflect the entire incident light. In addition, when the incident angle of the external light falls within a predetermined range, the optical rod 160a may pass the entire incident light. The optical rod 160a may pass only part of the external light incident on the adjustable intraocular lens 100 so that a clear image is formed on the retina. The optical rod 160a generates an effect similar to a pinhole effect, but the total amount of light passing through the optical rod 160a and the total area through which light passes are greatly increased, as compared to a conventional pinhole effect, so that a brighter and clearer image is generated on the retina.

Figure 5A:
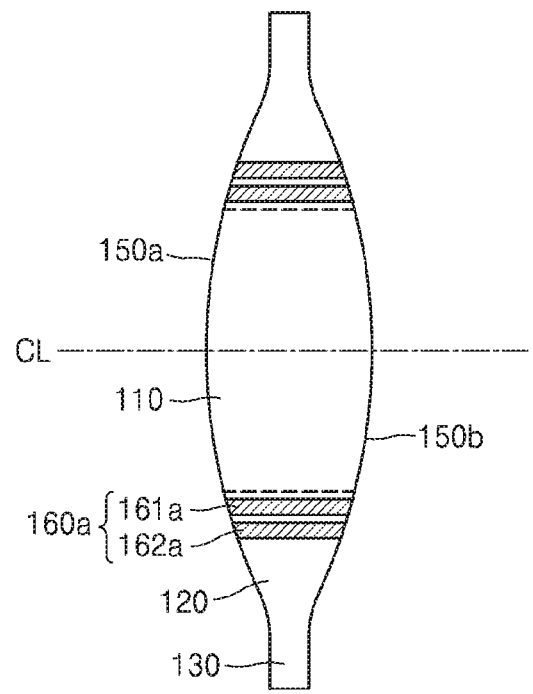
FIGS. 5A to 5F are cross-sectional views illustrating another modification of the adjustable intraocular lens of FIG. 1.
Figure 5B:
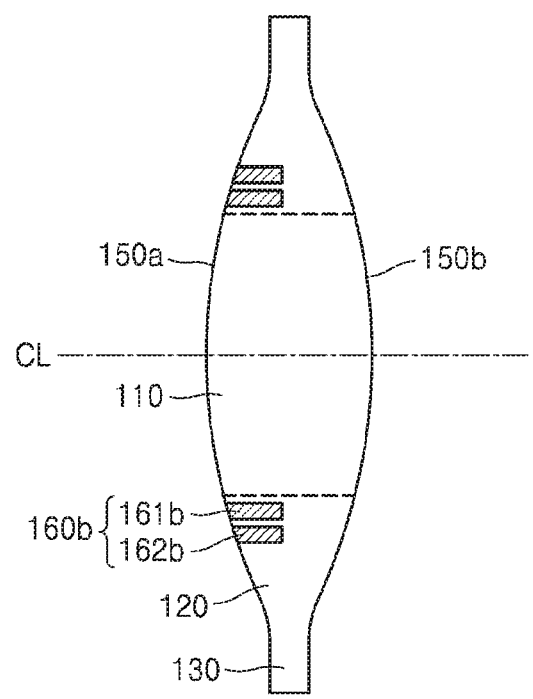

Referring to FIG. 5B, an optical rod 160b may be inserted into a front surface 150a. The optical rod 160b is inserted into the front surface 150a in the first direction at a predetermined length, and the optical rod 160b may not extend to a rear surface 150b.

For example, the optical rod 160b may include a first rod portion 161b and a second rod portion 162b, and may be inserted into the front surface 150a along the first direction at a predetermined length.

The optical rod 160b may selectively pass part of external light incident on a transition zone 120 of the front surface 150a. The optical rod 160b may reflect part of incident light and may pass part of the incident light according to a refractive index of the optical rod 160b. In addition, when an incident angle of the external light is equal to or greater than a critical angle of the optical rod 160b, the optical rod 160b may reflect the entire incident light. In addition, when the incident angle of the external light falls within a predetermined range, the optical rod 160b may pass the entire incident light. The optical rod 160b may pass only part of the external light incident on the adjustable intraocular lens 100 so that an image is clearly formed on a retina. The optical rod 160b generates an effect similar to a pinhole effect, but the total amount of light passing through the optical rod 160b and a total area through which light passes are greatly increased, as compared to a conventional pinhole effect, so that a brighter and clearer image is generated on the retina.

Figure 5C:
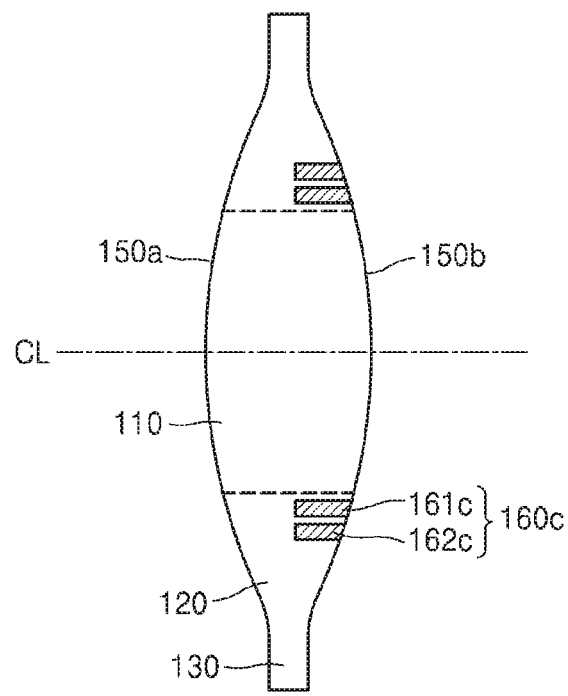

Referring to FIG. 5C, an optical rod 160c may be inserted into a rear surface 150b. The optical rod 160c is inserted into the rear surface 150b along the first direction at a predetermined length, and the optical rod 160c may not extend to a front surface 150a.

For example, the optical rod 160c may include a first rod portion 161c and a second rod portion 162c, and may be inserted into the rear surface 150b along the first direction at a predetermined length.

The optical rod 160c may selectively pass part of external light incident on a transition zone 120 of the front surface 150a. The external light is incident on the transition zone 120 and moves toward the optical rod 160c.

The optical rod 160c may selectively pass part of external light incident on the transition zone 120 of the front surface 150a. The optical rod 160c may reflect part of incident light and may pass part of the incident light according to a refractive index of the optical rod 160c. In addition, when an incident angle of the external light is equal to or greater than a critical angle of the optical rod 160c, the optical rod 160c may reflect the entire incident light. In addition, when the incident angle of the external light falls within a predetermined range, the optical rod 160c may pass the entire incident light. The optical rod 160c may pass only part of the external light incident on the adjustable intraocular lens 100 so that an image is clearly formed on a retina. The optical rod 160c generates an effect similar to a pinhole effect, but the total amount of light passing through the optical rod 160c and a total area through which light passes are greatly increased, as compared to a conventional pinhole effect, so that a brighter and clearer image is generated on the retina.

Figure 5D:
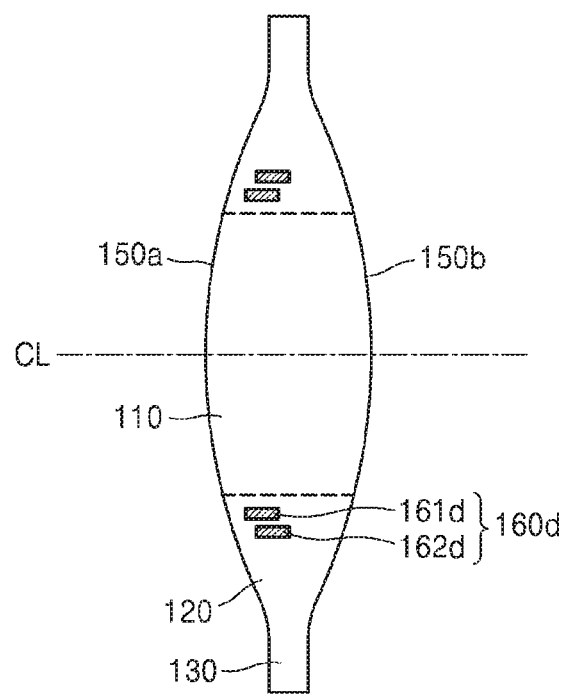

Referring to FIG. 5D, an optical rod 160d may be disposed inside a lens body 150. The optical rod 160d may be arranged adjacent to a front surface 150a of the lens body 150.

For example, the optical rod 160d may include a first rod portion 161d and a second rod portion 162d, each of which may be arranged within a transition zone 120 along the first direction. At this time, the first rod portion 161d and the second rod portion 162d may be arranged adjacent to the front surface 150a rather than a rear surface 150b.

The optical rod 160d can selectively pass part of external light incident on the transition zone 120 of the front surface 150a. The optical rod 160d may reflect part of incident light and may pass part of the incident light according to a refractive index of the optical rod 160d. In addition, when an incident angle of the external light is equal to or greater than a critical angle of the optical rod 160d, the optical rod 160d may reflect the entire incident light. In addition, when the incident angle of the external light falls within a predetermined range, the optical rod 160d may pass the entire incident light.

The optical rod 160d may pass only part of the external light incident on the adjustable intraocular lens 100 so that an image is clearly formed on a retina. The optical rod 160d generates an effect similar to a pinhole effect, but the total amount of light passing through the optical rod 160d and a total area through which light passes are greatly increased, as compared to a conventional pinhole effect, so that a brighter and clearer image is generated on the retina.

Figure 5E:
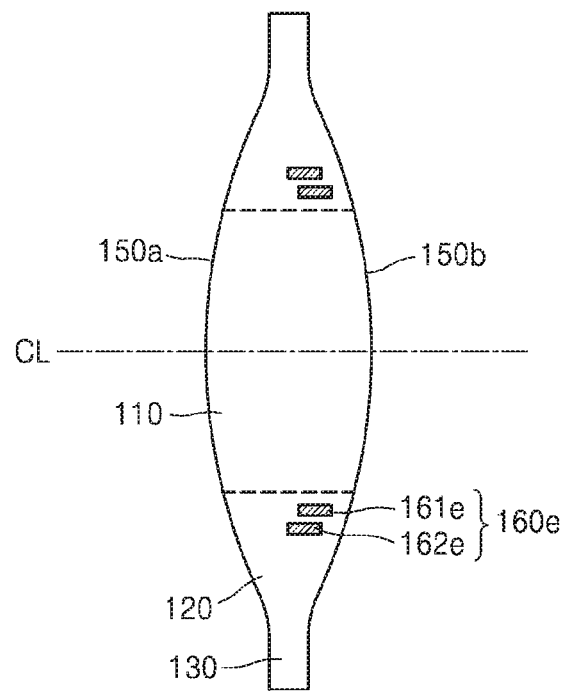

Referring to FIG. 5E, an optical rod 160e may be arranged inside a lens body 150. The optical rod 160e may be arranged adjacent to a rear surface 150b of the lens body 150.

For example, the optical rod 160e may include a first rod portion 161e and a second rod portion 162e, each of which may be arranged within a transition zone 120 along the first direction. At this time, the first rod portion 161e and the second rod portion 162e may be arranged adjacent to the rear surface 150b rather than a front surface 150a.

The optical rod 160e may selectively pass part of external light incident on the transition zone 120 of the front surface 150a. The optical rod 160e may reflect part of incident light and may pass part of the incident light according to a refractive index of the optical rod 160e. In addition, when an incident angle of the external light is equal to or greater than a critical angle of the optical rod 160e, the optical rod 160e may reflect the entire incident light. In addition, when the incident angle of the external light falls within a predetermined range, the optical rod 160e may pass the entire incident light. The optical rod 160e may pass only part of the external light incident on the adjustable intraocular lens 100 so that an image is clearly formed on a retina. The optical rod 160e generates an effect similar to a pinhole effect, but the total amount of light passing through the optical rod 160e and a total area through which light passes are greatly increased, as compared to a conventional pinhole effect, so that a brighter and clearer image is generated on the retina.

Figure 5F:
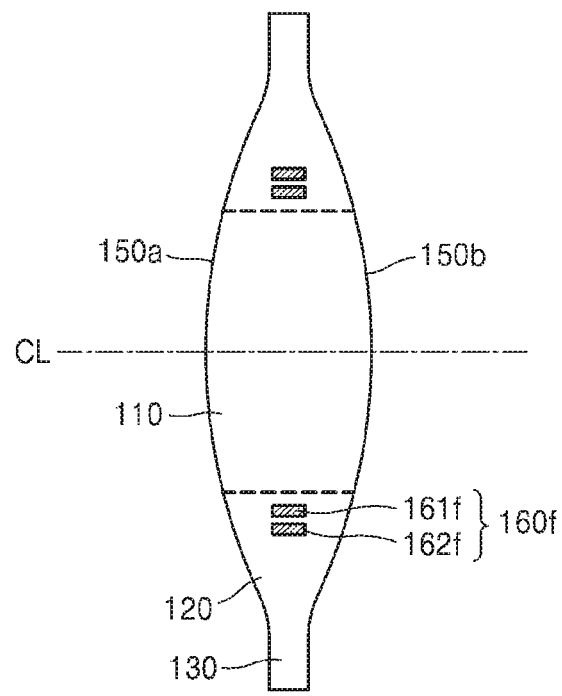

Referring to FIG. 5F, an optical rod 160f may be arranged inside a lens body 150. The optical rod 160f may be arranged at the center of the thickness of the lens body 150.

For example, the optical rod 160f may include a first rod portion 161f and a second rod portion 162f, each of which may be arranged within a transition zone 120 along the first direction. At this time, the first rod portion 161f and the second rod portion 162f may be arranged between a front surface 150a and a rear surface 150b.

Figure 6:
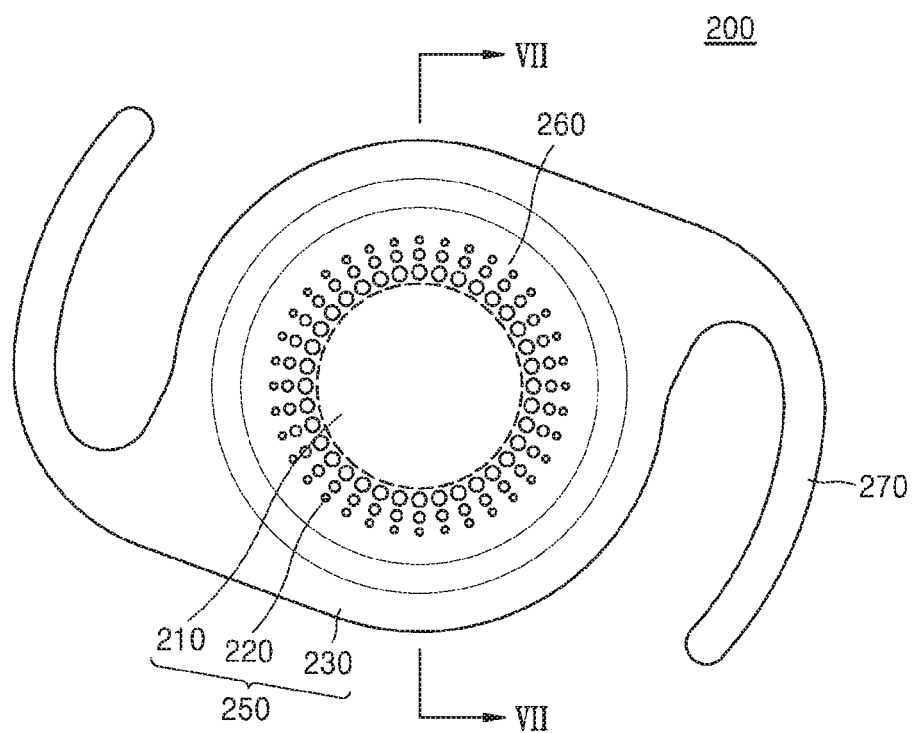
FIG. 6 is a plan view illustrating an adjustable intraocular lens according to another aspect of the presently disclosed embodiment.
Figure 7:
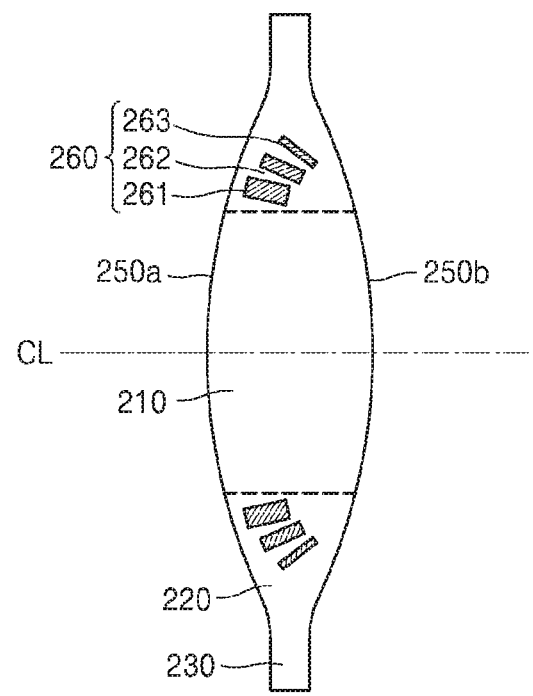
FIG. 7 is a cross-sectional view taken along a line VII-VII of FIG. 6.

FIG. 6 is a plan view illustrating an adjustable intraocular lens 200 according to another aspect of the presently disclosed embodiment, and FIG. 7 is a cross-sectional view taken along a line VII-VII of FIG. 6.

Referring to FIGS. 6 to 7, the adjustable intraocular lens 200 may include a lens body 250, a support portion 270, and an optical rod 260. The lens body 250 may include a central optic zone 210, a transition zone 220, and an edge zone 230. However, another aspect of the presently disclosed embodiment characteristically differs from the above-described aspect in terms of the shape and arrangement of the optical rod 260. Therefore, in the description of the presently disclosed embodiment, portions not described herein will quote the description of the above-mentioned aspect, and the description thereof will not be explained in detail.

A plurality of optical rods 260 may be arranged in a radial direction of a central optic zone 210, and diameters of the optical rods 260 may be reduced in the radial direction. Hereinafter, for convenience of description, a case where three rod portions are formed will be described.

Specifically, the optical rod 260 may include a first rod portion 261 adjacent to the central optic zone 210 and arranged in a circular shape around the central optic zone 210, and a second rod portion 262 arranged on the outside in the radial direction of the first rod portion 261. In addition, the optical rod 260 may include a third rod portion 263 arranged on the outside in the radial direction of the second rod portion 262. The diameter of the first rod portion 261 arranged closest to the central optic zone 210 may be largest and the diameter of the third rod portion 263 arranged at the outermost portion of the central optic zone 210 may be smallest.

A longitudinal direction of the optical rod 260 may have a predetermined angle with the first direction. The optical rod 260 may form a predetermined angle with a center line CL of the central optic zone 210. In addition, the angle may increase in the radial direction of the central optic zone 210. External light incident on the central optic zone 210 may pass through the central optic zone 210 to form an image on a retina. In addition, the light passing through the central optic zone 210 may adjust the formed image to be brighter.

A plurality of optical rods 260 may be arranged in the radial direction of the central optic zone, and the diameters of the optical rods may be reduced in the radial direction. When the diameter of the first rod portion 261 is designed to be large, the amount of aligned light toward the macula, which is a structure in the retina forming the center of a visual axis, may be further secured. Aligning the light may increase the depth of focus and by securing the maximum amount of aligned light, the adjustable intraocular lens 200 which projects a much brighter and clearer image on retina may be provided. When the diameter of the third rod portion 263 is reduced, the density of optical rods included in the same area can be increased to effectively block the light which is incident at a larger incident angle toward the outside of the adjustable intraocular lens 200, the light disturbing improvement of the depth of focus.

In another aspect, when the diameter of the first rod portion 261 is reduced, the area occupied by the first rod portion 261 in the transition zone 220 is reduced. Therefore, light incident on the transition zone 220 is relatively increased. Since the first rod portion 261 is arranged adjacent to the central optic zone 210, the amount of light incident on a region near the central optic zone 210 may be increased and the amount of light incident on a region farther from the central optic zone 210 may be reduced. Thus, the adjustable intraocular lens 200 with improved brightness may be provided.

FIGS. 8A to 8G are cross-sectional views illustrating modifications of the adjustable intraocular lens of FIG. 6. Modifications of the adjustable intraocular lens 200 are characteristically different in terms of the structure and arrangement of the optical rod, and a description thereof will be described.

Figure 8A:
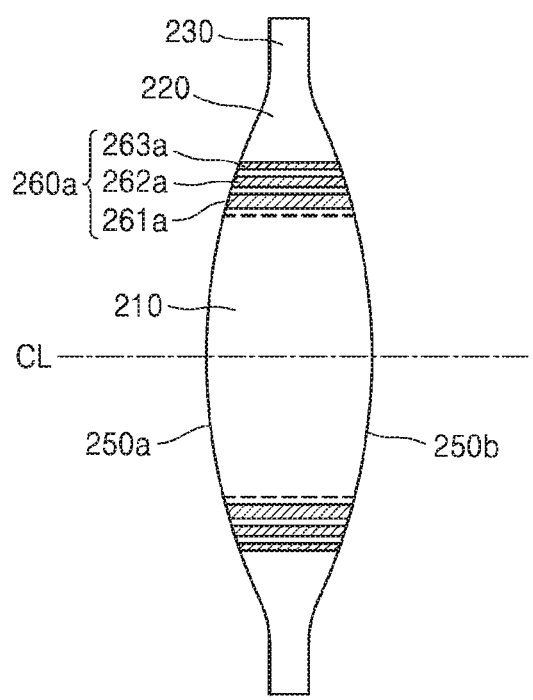
FIGS. 8A to 8G are cross-sectional views illustrating modifications of the adjustable intraocular lens of FIG. 6.

Referring to FIG. 8A, an optical rod 260a may be inserted to connect a front surface 250a to a rear surface 250b. For example, the optical rod 260a may include a first rod portion 261b, a second rod portion 262b, and a third rod portion 263c, each of which may extend from the front surface 250a to the rear surface 250b in the first direction. The diameter of the first rod portion 261a arranged closest to the central optic zone 210 may be largest and the diameter of the third rod portion 263c arranged at the outermost portion of the central optic zone 210 may be smallest.

Figure 8B:
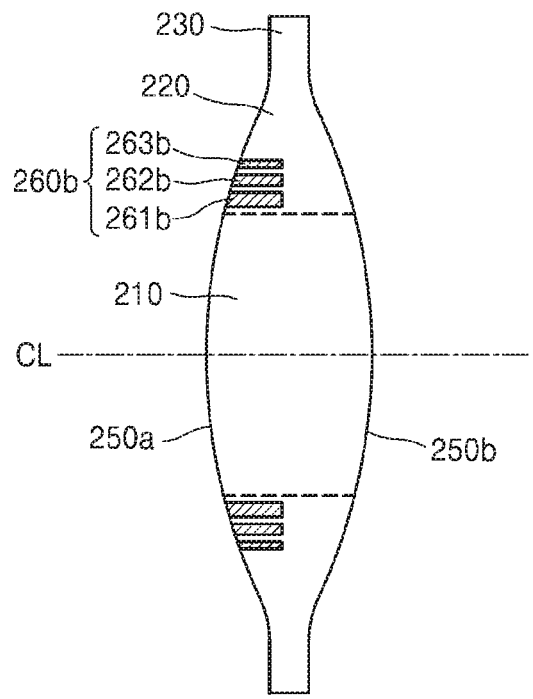

Referring to FIG. 8B, the optical rod 260b may be inserted into the front surface 250a. The optical rod 260b may be inserted into the front surface 250a along the first direction at a predetermined length, and the optical rod 260b may not extend to the rear surface 250b.

For example, the optical rod 260b may include a first rod portion 261b, a second rod portion 262b, and a third rod portion 263c, each of which may be inserted into the front surface 250a along the first direction. The diameter of the first rod portion 261b arranged closest to the central optic zone 210 may be largest and the diameter of the third rod portion 263b arranged at the outermost portion of the central optic zone 210 may be smallest.

Figure 8C:
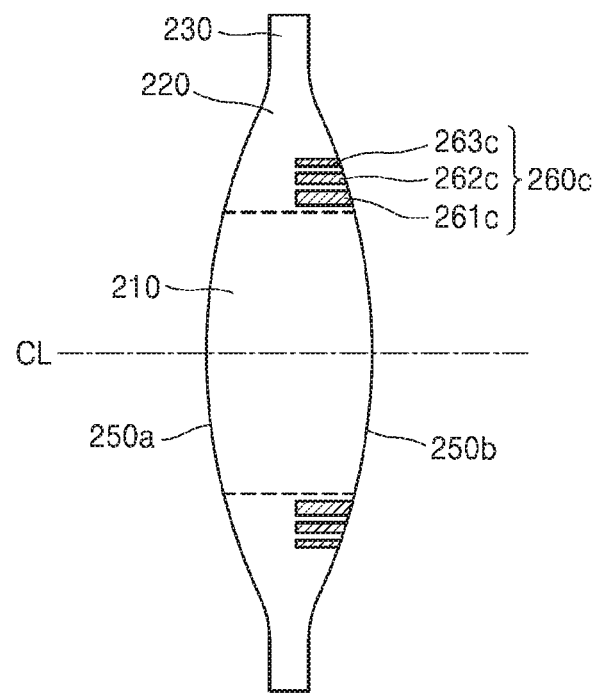

Referring to FIG. 8C, an optical rod 160c may be inserted into a rear surface 250b. The optical rod 260c may be inserted into the rear surface 250b along the first direction at a predetermined length, and the optical rod 260c may not extend to a front surface 250a.

For example, the optical rod 260c may include a first rod portion 261c, a second rod portion 262c, and a third rod portion 263c, each of which may be inserted into a rear surface 250b in the first direction. The diameter of the first rod portion 261c arranged closest to the central optic zone 210 may be largest and the diameter of the third rod portion 263c arranged at the outermost portion of the central optic zone 210 may be smallest.

Figure 8D:
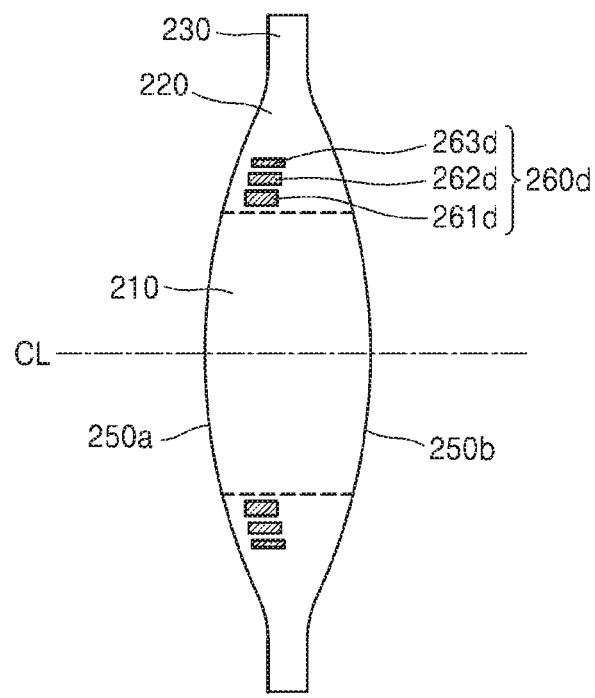

Referring to FIG. 8D, an optical rod 260d may be disposed inside a lens body 250. The optical rod 260d may be arranged adjacent to a front surface of the lens body 250.

For example, the optical rod 260d may include a first rod portion 261d, a second rod portion 262d, and a third rod portion 263d, each of which may be arranged within the transition zone 220 along the first direction. At this time, the first rod portion 261d, the second rod portion 262d, and the third rod portion 263d may be arranged adjacent to a front surface 250a rather than a rear surface 250b.

In addition, the diameter of the first rod portion 261d arranged closest to a central optic zone 210 may be largest and the diameter of the third rod portion 263d arranged at the outermost portion of the central optic zone 210 may be smallest.

Figure 8E:
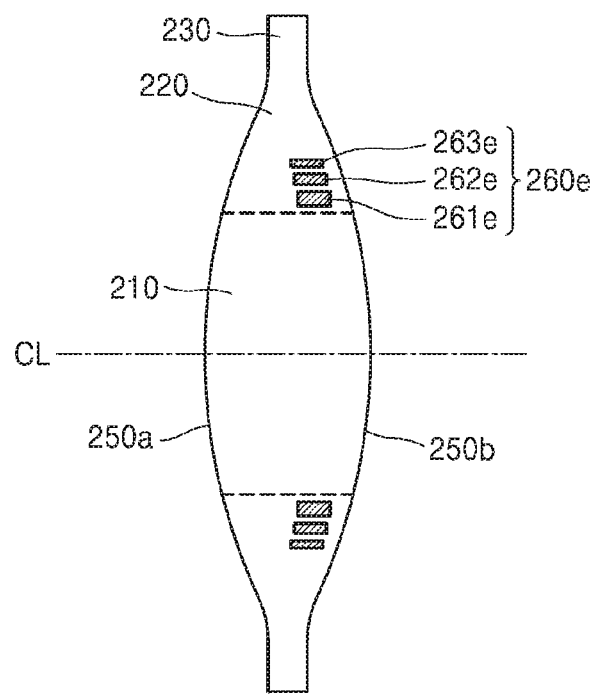

Referring to FIG. 8E, an optical rod 260e may be arranged inside a lens body 250. The optical rod 260e may be arranged adjacent to a rear surface 250b of the lens body 250.

For example, the optical rod 260e may include a first rod portion 261e, a second rod portion 262e, and a third rod portion 263e, each of which may be arranged within the transition zone 220 in the first direction. At this time, the first rod portion 261e, the second rod portion 262e, and the third rod portion 263e may be arranged adjacent to a rear surface 250b rather than a front surface 250a.

In addition, the diameter of the first rod portion 261e arranged closest to a central optic zone 210 may be largest and the diameter of the third rod portion 263e arranged at the outermost portion of the central optic zone 210 may be smallest.

Figure 8F:
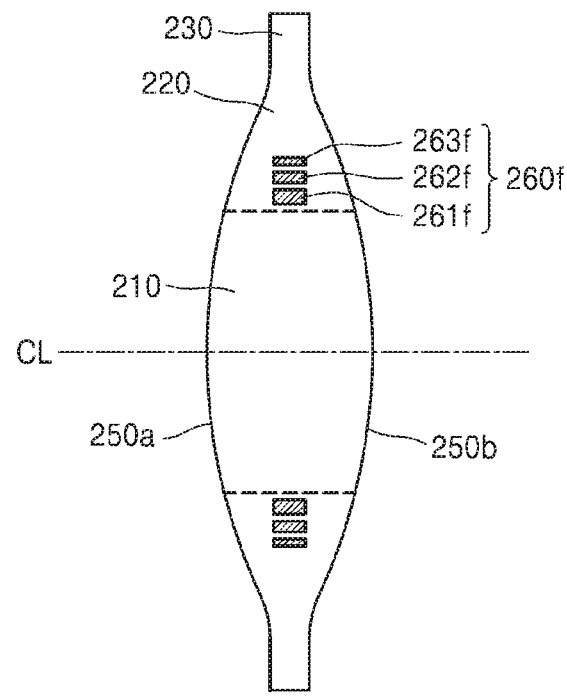

Referring to FIG. 8F, an optical rod 160f may be arranged inside a lens body 250. The optical rod 260f may be arranged at the center of the thickness of the lens body 250.

For example, the optical rod 260f may include a first rod portion 261f, a second rod portion 262f, and a third rod portion 263f, each of which may be arranged within the transition zone 220 in the first direction. At this time, the first rod portion 261f and the second rod portion 262f may be arranged between a front surface 250a and a rear surface 250b.

Figure 8G:
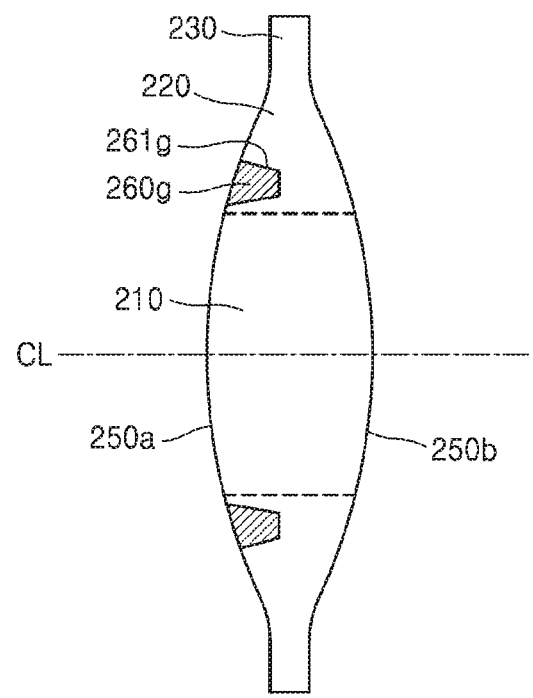

FIG. 8G is a cross-sectional view illustrating another modification of the adjustable intraocular lens 200 of FIG. 6. The modification of the adjustable intraocular lens 200 is characteristically different in terms of the structure and arrangement of the optical rod, and a description thereof will be described.

An optical rod 260g may have a tapered outer wall 261g. The optical rod 260g may have the outer wall 261g tapered in the first direction. Specifically, a cross-section of the optical rod 260g is large on a front surface 250a and is reduced toward a rear surface 250b. Part of light incident on the optical rod 260g may strike the tapered outer wall 261g. That is, part of light passing through the optical rod 260g may strike the outer wall 261g again to reduce the amount of light transmitted through the optical rod 260g. Even if the volume of the optical rod 260g is reduced by the tapered outer wall 261g, the optical rod 260g may effectively reflect the incident light again and align the light.

Figure 9:
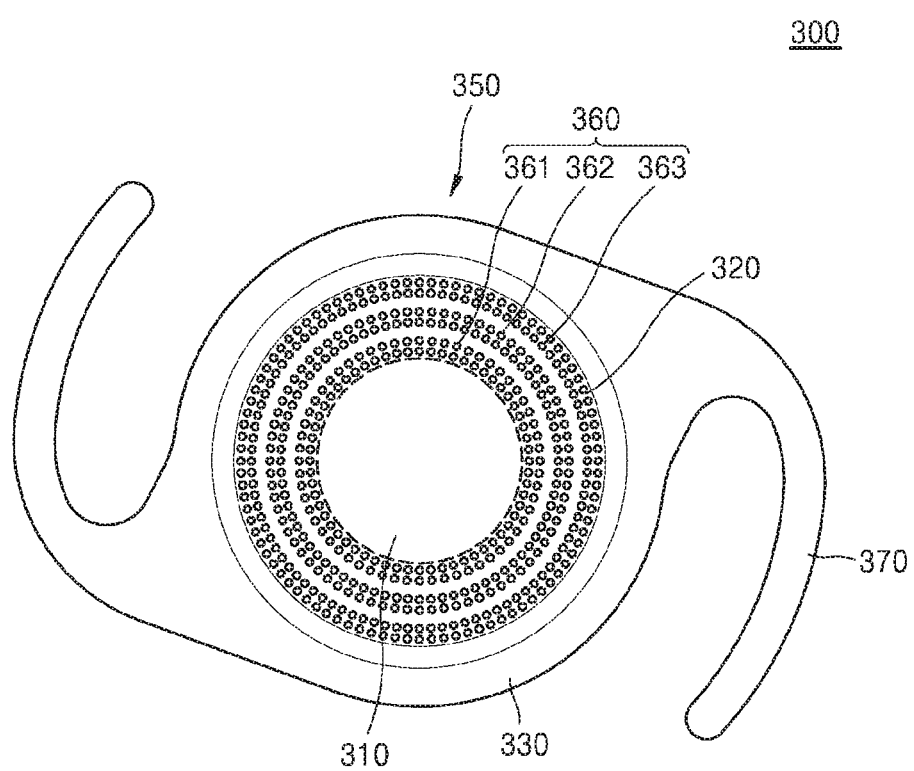
FIG. 9 is a plan view illustrating an adjustable intraocular lens according to another aspect of the presently disclosed embodiment.

FIG. 9 is a perspective view illustrating an adjustable intraocular lens 300 according to another aspect of the presently disclosed embodiment.

Referring to FIG. 9, the adjustable intraocular lens 300 may include a lens body 350, a support portion 370, and an optical rod 360. The lens body 350 may include a central optic zone 310, a transition zone 220, and an edge zone 330. However, another aspect of the presently disclosed embodiment characteristically differs from the above-described aspect in terms of the shape and arrangement of the optical rod 360. Therefore, in the description of the presently disclosed embodiment, portions not described herein will quote the description of the above-mentioned aspect, and the description thereof will not be explained in detail.

The optical rod 360 may form a plurality of bands. The optical rod 360 may be arranged in the transition zone 320 and may be arranged with a predetermined interval in a radial direction. The number of bands including the optical rod 360 is not limited to a specific number. Hereinafter, for convenience of description, a case where three bands are formed will be described.

Specifically, the optical rod 360 may include a first rod band 361 arranged on an outer side of a central optic zone 310, a second rod band 362 arranged on an outer side of the first rod band 361, and a third rod band 363 arranged on an outside of the second rod band 362. The first rod band 361 and the second rod band 362 may be arranged with a predetermined interval, and the second rod band 362 and the third rod band 363 may be arranged with a predetermined interval. Each of the rod bands may have a predetermined angle with a center line CL of the lens body 350, or may contact with any one of the surfaces. In addition, each of the rod bands may be arranged adjacent to one side of the lens body 350 while having a gap therebetween, and may be arranged at the center of the lens body 350. The description thereof will quote the description of the above-mentioned aspect.

The adjustable intraocular lens 300 may increase the amount of light incident at intervals between the rod bands, thereby securing the field of view. That is, the field of view may be widened by external light passing through the gap between the rod bands.

Figure 10A:
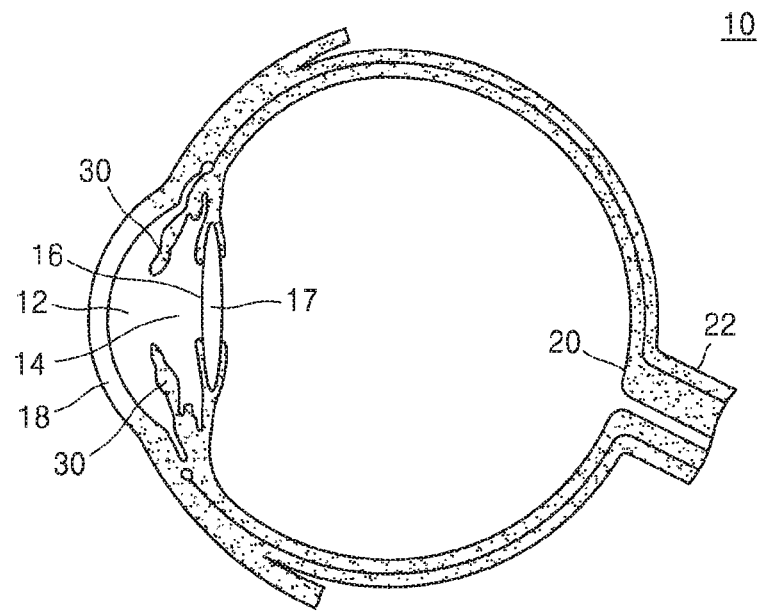
FIG. 10A is a cross-sectional view of a human eye illustrating a natural lens.
Figure 10B:
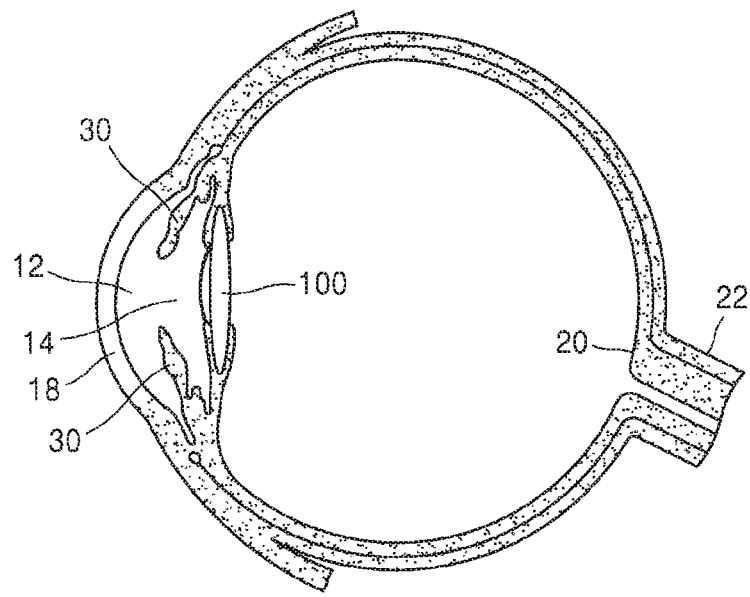
FIG. 10B is a cross-sectional view of a human eye into which an adjustable intraocular lens is inserted.

FIG. 10A is a cross-sectional view of a human eye 10 illustrating a natural lens, and FIG. 10B is a cross-sectional view of the human eye 10 into which an adjustable intraocular lens is inserted.

FIG. 10A illustrates a cross-sectional view of the human eye 10 having a front chamber 12 and a rear chamber 14 that are separated by an iris 30. In the rear chamber 14, a lens capsule 16 holding a natural lens 17 of an eye is present. Light entering the eye passes through a cornea 18 and travels to the lens 17, and the cornea 18 and the lens 17 serve to direct the light to an image on a retina 20 located at the back of the eye and adjust focus. The retina 20 is connected to an optic nerve 22, and the optic nerve 22 transfers the image received by the retina 20 to a brain for the purpose of analysis.

The natural lens 17 can no longer properly focus or direct the incident light to the retina in a damaged eye 10 (for example, blurred by cataract), and the image is blurred. A well-known surgical technique for treating this condition includes removing the damaged lens and replacing the damaged lens with an artificial lens such as an intraocular lens.

Referring to FIG. 10B, a surgeon may cut out all or part of the natural lens 17 and implant the adjustable intraocular lens 100. At this time, the central optic zone 110 may be aligned to be positioned to face the macula. The support portion 170 may be fixed at an appropriate position in the lens capsule so that the lens body 150 does not move.

Figure 11:
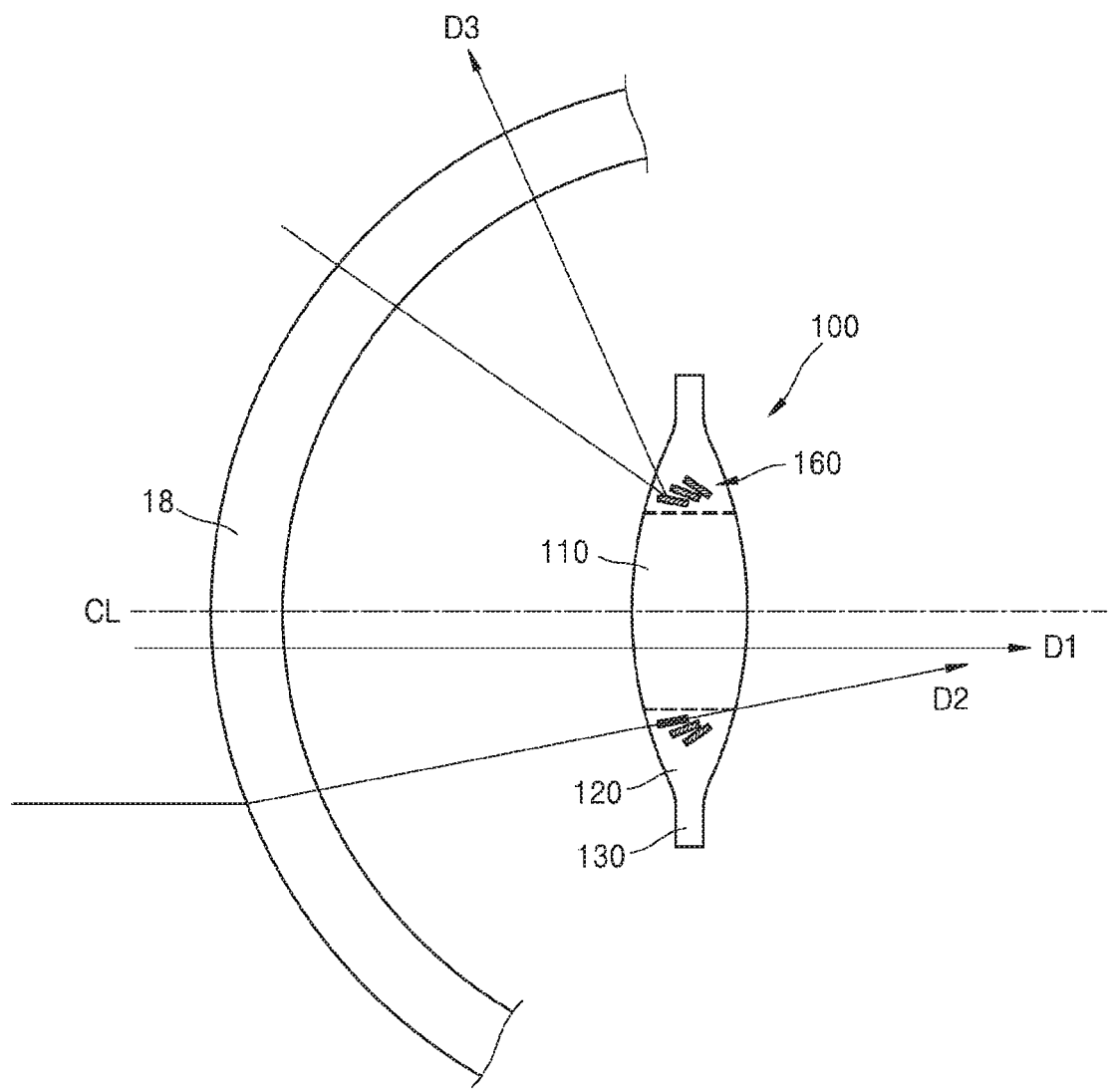
FIG. 11 is a conceptual diagram illustrating incidence of external light on the adjustable intraocular lens of FIG. 1.

FIG. 11 is a conceptual diagram illustrating incidence of external light on the adjustable intraocular lens 100 of FIG. 1.

Referring to FIG. 11, it can be seen that the adjustable intraocular lens 100 is implanted in the eye and the a clear image is generated on the retina When viewing an object from a medium or near distance, a conventional multifocal intraocular lens produces unfocused light, which causes flashes or halos, resulting in visual disturbance. This is related to the property of light that travels straight. Most of light incident from a long distance is vertically incident on the retina 20, but light incident from near distance has various incident angles and only part of the light is vertically incident on the retina 20. That is, when viewing an object at a medium or near distance, a plurality of images are formed on the retina due to light having different incident angles, resulting in visual disturbance.

The adjustable intraocular lens 100 may form a clear image on the retina by aligning light incident at a near distance or a medium distance.

D1 indicates light incident from a long distance, and D2 and D3 indicate light incident from a near distance or a medium distance. D2 indicates light that passes through the optical rod 160, and D3 indicates light reflected from the sidewall of the optical rod 160 due to a large incident angle.

Light incident from a long distance like D1 vertically enter the cornea 18, the central optic zone 110, or the optical rod 160 and pass therethrough. That is, most of the light incident from a long distance may pass through the adjustable intraocular lens 100.

Light may pass through the optical rod 160 when light having a small incident angle is incident from a near distance or a medium distance like D2, that is, when light is incident almost perpendicular to the adjustable intraocular lens. Light having a small incident angle passes through both the central optic zone 110 and the optical rod 160, thereby improving the depth of focus.

Meanwhile, when light having a large incident angle is incident from a near distance or a medium distance like D3, light may be reflected by the optical rod 160. That is, when the incident angle of light directed to the adjustable intraocular lens 100 is large, the light directed toward the central optic zone 110 passes though the central optic zone 110, but the light directed toward the optical rod 160 is reflected because the refractive index of the optical rod 160 is different from that of the central optic zone 110.

In particular, the light may be reflected from the side of the optical rod 160. Since the refractive index of the optical rod 160 is different from that of the transition zone 120, light having a large incident angle passes through the transition zone 120 and is reflected by a difference in refractive index at the side of the optical rod 160.

In addition, a light absorbing coating or the like may be applied to the side surface of the optical rod 160. Light having a large incident angle may pass through the transition zone 120, or may be absorbed through the coating on the side surface of the optical rod 160.

The adjustable intraocular lens 100 selectively passes only a part of incident light, thereby improving the depth of focus by aligning light in the optical rod 160. That is, the optical rod 160 generates an effect similar to the pinhole effect so that a clear image may be formed on the retina.

The adjustable intraocular lens 100 transmits light incident on the central optic zone 110, but selectively transmits light incident on the optical rod 160, thereby forming a clear image.

The adjustable intraocular lens 100 may align light by the optical rod 160 and minimize mutual interference of light, thereby improving the depth of focus.

The adjustable intraocular lenses 200 and 300 may adjust the amount of light passing through the central optic zones 210 and 310, thereby adjusting the brightness of the image formed on the retina.

Although the presently disclosed embodiment has been described in connection with the above-mentioned preferred aspects, it is possible to make various modifications and changes without departing from the spirit and scope of the disclosed embodiment. Therefore, it is intended that the appended claims cover such modifications and changes falling within the spirit and scope of the disclosed embodiment.

According to an aspect of the presently disclosed embodiment, an adjustable intraocular lens is provided to improve the depth of focus, and aspects of the presently disclosed embodiment are applicable to lenses, glasses, spectacles, and the like, to which the adjustable intraocular lens for industrial use is applied.

What is claimed is:

1. An adjustable intraocular lens comprising:
   a lens body having a front surface and a rear surface and comprising a central optic zone formed convexly in a first direction;
   a plurality of support portions extending from an edge of the lens body in a radial direction; and
   an optical rod arranged so that at least part thereof is included inside the lens body and the optical rod arranged at an outer portion of the central optic zone,
   wherein external light directed to the central optic zone passes through the central optic zone, and the external light directed to the optical rod selectively passes through the optical rod according to an incidence angle of the external light.

2. The adjustable intraocular lens of claim 1, wherein a refractive index of the optical rod is different from a refractive index of the central optic zone.

3. The adjustable intraocular lens of claim 1, wherein the optical rod is arranged so that a length direction of the optical rod and the first direction form a predetermined angle.

4. The adjustable intraocular lens of claim 1, wherein the lens body comprises:
   a transition zone which surrounds the central optic zone and in which the optical rod is arranged; and
   an edge zone which surrounds the transition zone and to which the plurality of support portions are connected.

5. The adjustable intraocular lens of claim 4, wherein a thickness of the transition zone in the first direction is gradually reduced from the central optic zone toward the edge zone.

6. The adjustable intraocular lens of claim 1, wherein the optical rod comprises:
   a first rod portion arranged at an outer side of the central optic zone; and
   a second rod portion arranged adjacent to the first rod portion in a radial direction,
   wherein the first rod portion comprises a plurality of first rods spaced apart from each other to surround the central optic zone,
   wherein the second rod portion comprises a plurality of second rods spaced apart from each other to surround the first rod portion, wherein the second rods are spaced apart from the first rods in a radial direction.

7. The adjustable intraocular lens of claim 6, wherein an angle formed by the length direction of the first rod portion and the first direction is less than an angle formed by a length direction of the second rod portion and the first direction.

8. The adjustable intraocular lens of claim 1, wherein a plurality of optical rods are arranged in a radial direction of the central optic zone, and diameters of the optical rods are reduced in the radial direction.

9. The adjustable intraocular lens of claim 1, wherein the optical rod extends from the front surface to the rear surface of the lens body.

10. The adjustable intraocular lens of claim 1, wherein the optical rod is inserted into the front surface or the rear surface of the lens body.

11. The adjustable intraocular lens of claim 1, wherein the optical rod is arranged inside the lens body.

12. The adjustable intraocular lens of claim 11, wherein the optical rod is arranged such that a first distance between an end of the optical rod and the front surface of the lens body is longer or shorter than a second distance between the other end of the optical rod and the rear surface of the lens body.

13. The adjustable intraocular lens of claim 1, wherein an outer wall of the optical rod is tapered in a longitudinal direction of the optical rod.

14. The adjustable intraocular lens of claim 1, wherein the optical rod comprises at least one of a glass rod and an optical fiber.

15. The adjustable intraocular lens of claim 1, wherein at least some external light incident on the optical rod is totally reflected from an inner wall of the optical rod.

16. The adjustable intraocular lens of claim 1, wherein the external light passing through the optical rod is aligned towards a central axis of the central optic zone.

17. The adjustable intraocular lens of claim 1, wherein a light absorbing coating is applied to an outer wall of the optical rod.

18. An adjustable intraocular lens comprising:
   a lens body having a front surface and a rear surface and comprising a central optic zone formed convexly in a first direction; and
   an optical rod arranged so that at least part thereof is included inside the lens body and the optical rod being arranged at an outer portion of the central optic zone;
   wherein external light directed to the central optic zone passes through the central optic zone, and the external light directed to the optical rod selectively passes through the optical rod according to an incidence angle of the external light.

* * * * *